(12) United States Patent
Feiweier

(10) Patent No.: US 8,954,202 B2
(45) Date of Patent: Feb. 10, 2015

(54) OPERATING METHOD FOR A COMPUTER TO DETERMINE OPTIMIZED CONTROL SEQUENCES FOR AN IMAGING MEDICAL SYSTEM

(71) Applicant: Thorsten Feiweier, Poxdorf (DE)

(72) Inventor: Thorsten Feiweier, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 168 days.

(21) Appl. No.: 13/690,043

(22) Filed: Nov. 30, 2012

(65) Prior Publication Data

US 2013/0090776 A1   Apr. 11, 2013

Related U.S. Application Data

(63) Continuation of application No. 12/407,853, filed on Mar. 20, 2009, now abandoned.

(30) Foreign Application Priority Data

Mar. 20, 2008  (DE) .......................... 10 2008 015 261

(51) Int. Cl.
*G05B 19/02* (2006.01)
*A61B 6/00* (2006.01)
*G01R 33/54* (2006.01)
*G06F 19/00* (2011.01)
*A61B 5/055* (2006.01)
*A61B 8/00* (2006.01)

(52) U.S. Cl.
CPC ................ *G05B 19/02* (2013.01); *A61B 6/586* (2013.01); *G01R 33/54* (2013.01); *G06F 19/327* (2013.01); *A61B 5/055* (2013.01); *A61B 6/00* (2013.01); *A61B 8/00* (2013.01); *G01R 33/543* (2013.01)
USPC .......... 700/295; 700/22; 455/115.1; 324/309; 424/489

(58) Field of Classification Search
CPC ...................................................... G05B 19/02
USPC .................. 700/295, 22; 455/115.1; 324/309; 424/489
See application file for complete search history.

(56) References Cited

U.S. PATENT DOCUMENTS

| | | |
|---|---|---|
| 2003/0080738 A1 | 5/2003 | Brinker et al. |
| 2005/0197077 A1 | 9/2005 | Bielmeier et al. |
| 2006/0269612 A1 | 11/2006 | Xiang et al. |
| 2006/0274877 A1 | 12/2006 | Noshi et al. |

*Primary Examiner* — Tejal Gami
(74) *Attorney, Agent, or Firm* — Schiff Hardin LLP

(57) ABSTRACT

A computer is supplied with information about a measurement sequence to be implemented by a medical imaging system, and determines at least one group of preliminary control sequences for power supply devices of the medical imaging system so that the power control devices are caused to control image-influencing emission devices of the imaging medical system corresponding to the control sequences. Using a model of the image-influencing emission devices and their respective power control devices, and their respective initial load state, the computer determines whether a load state curve for those devices is below a load limit, and emits a final control sequence for those devices that are determined to be below the limit.

19 Claims, 8 Drawing Sheets

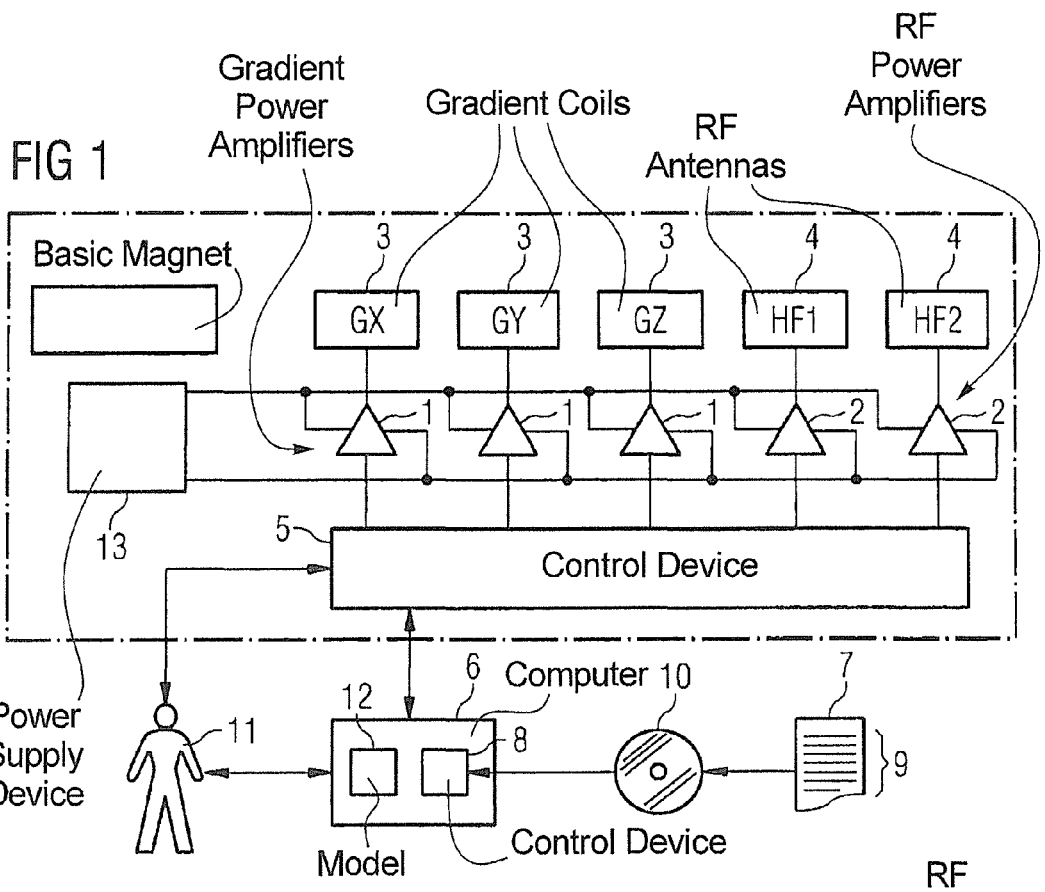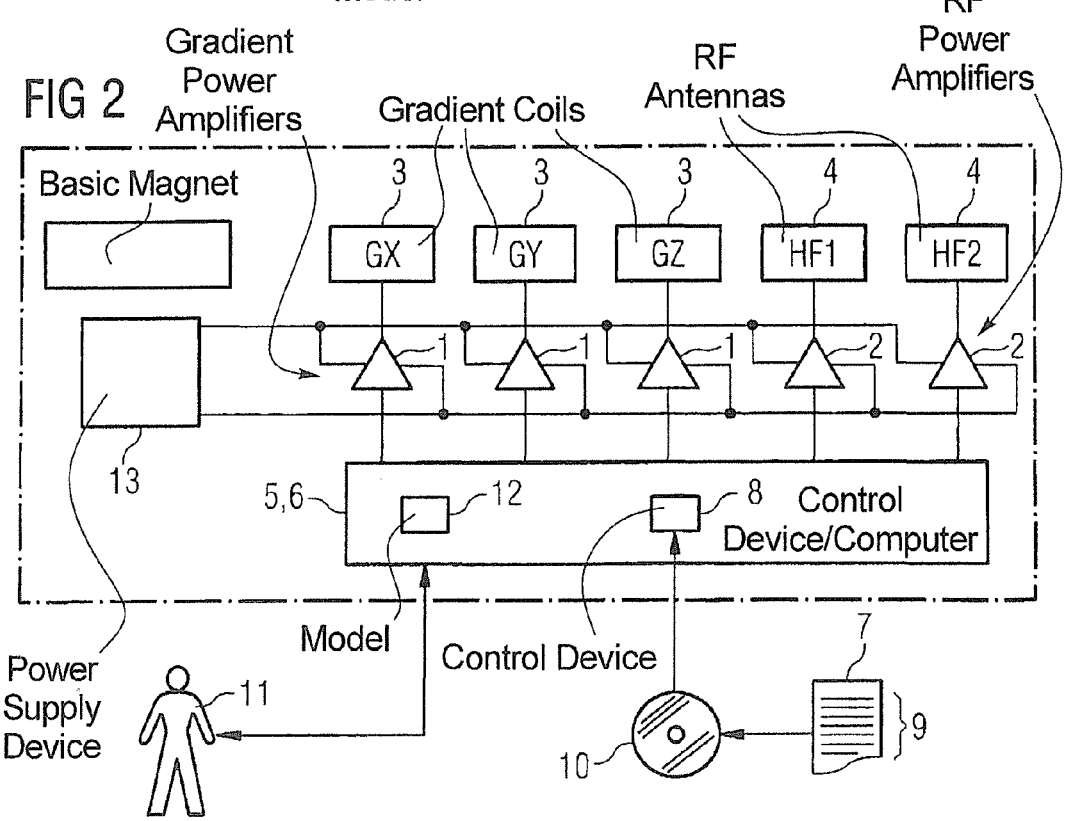

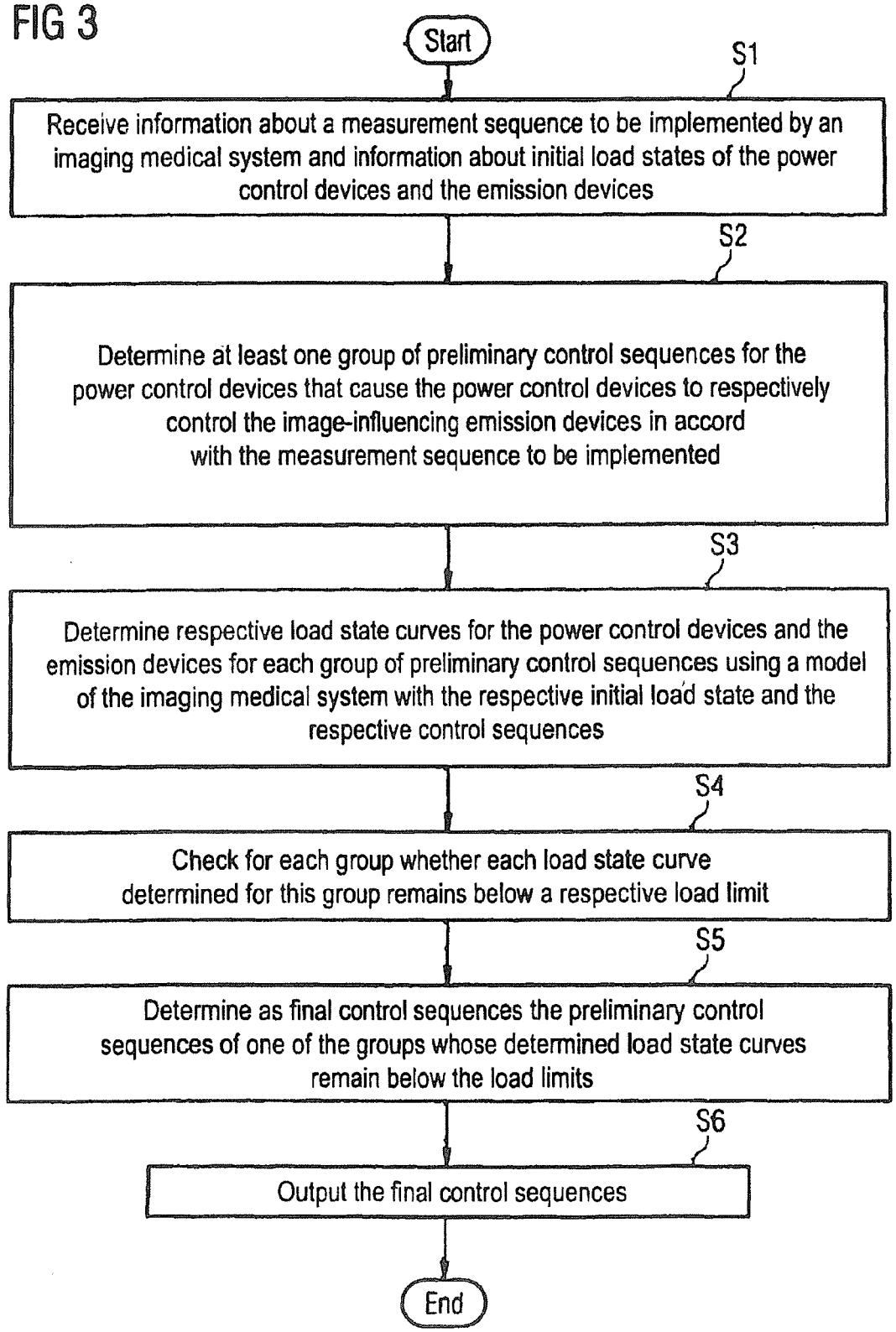

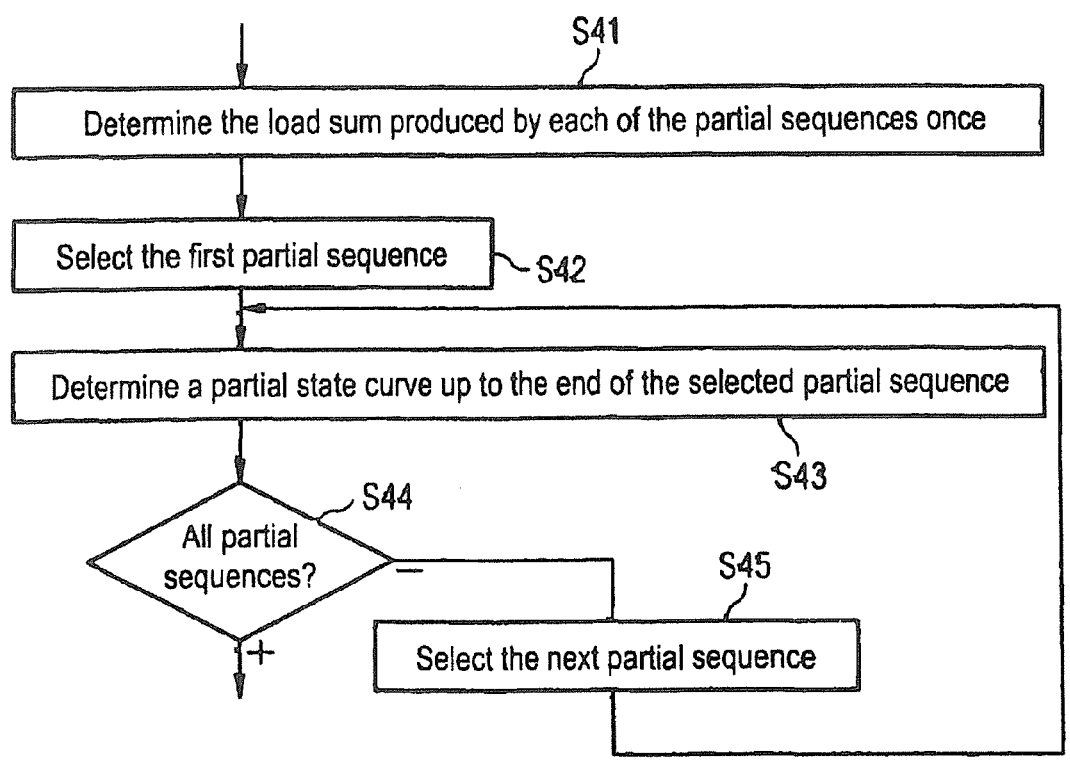

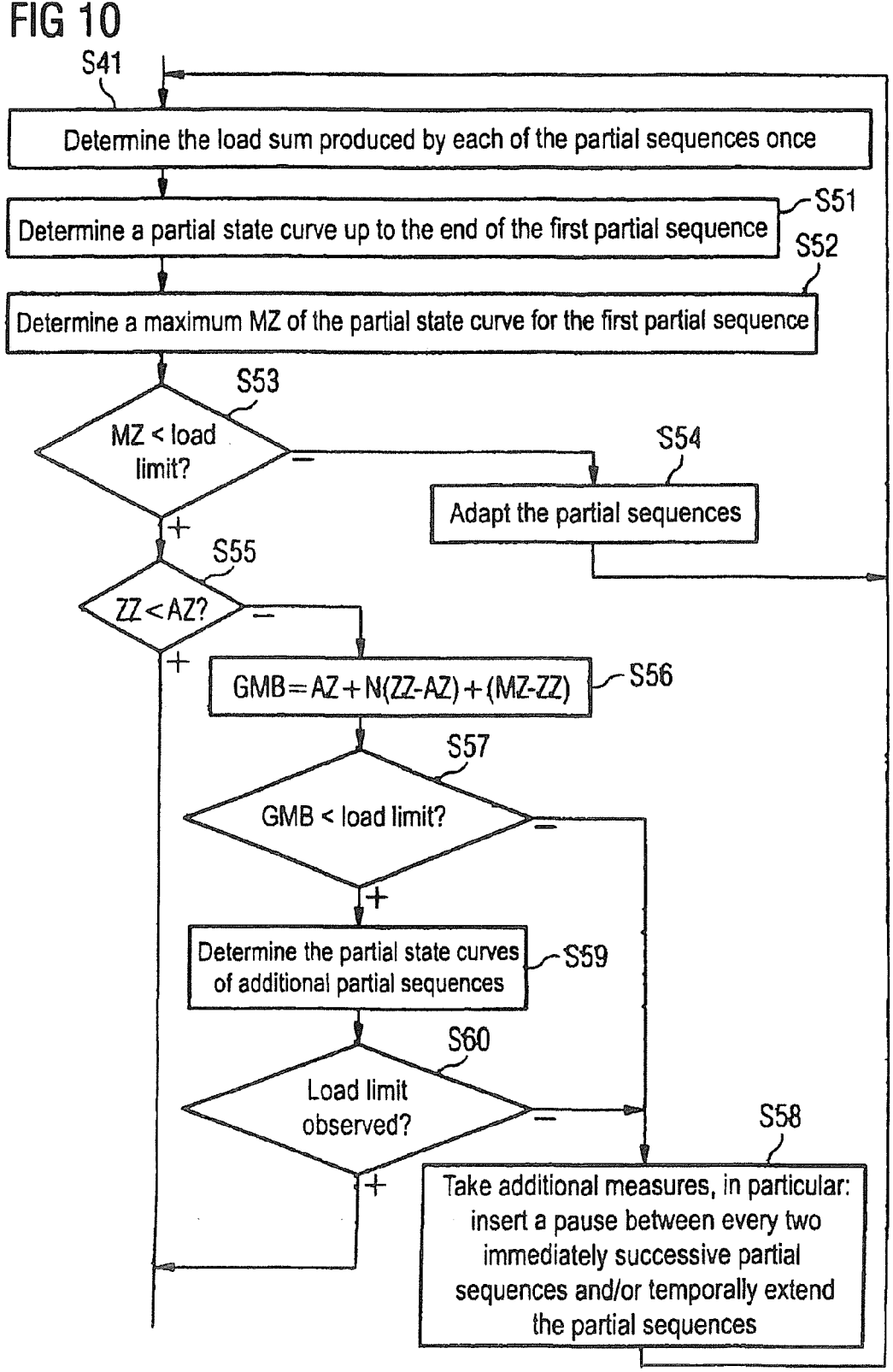

OPERATING METHOD FOR A COMPUTER TO DETERMINE OPTIMIZED CONTROL SEQUENCES FOR AN IMAGING MEDICAL SYSTEM

RELATED APPLICATION

The present application is a continuation of application Ser. No. 12/407,853, filed Mar. 20, 2009.

BACKGROUND OF THE INVENTION

1. Field of the Invention

The present invention concerns an operating method for a computer of the type wherein the computer receives information about a measurement sequence to be implemented by an imaging medical system, wherein the computer determines a group of control sequences for power control devices of the imaging medical system, and wherein the computer determines the control sequences to cause the power control devices to control (activate) image-influencing emission devices of the imaging medical system corresponding to the determined control sequences, in accordance with the measurement sequence to be implemented and outputs the control sequences to the power control devices.

The present invention furthermore concerns a computer-readable medium encoded with programming instructions that (machine code) that can be directly executed by a computer, wherein the execution of the machine code by the computer causes the computer to operate according to an operating method of the above type.

The present invention also concerns an imaging medical system of the type having power control devices and image-influencing emission devices controlled by the power control devices, a control device connected with at least the power control devices, and wherein the control device is either fashioned as a computer of the type described above or is connected with such a computer.

2. Description of the Prior Art

Methods and medical imaging systems of the general type noted above are known.

Limitations of hardware components of imaging medical systems have a significant influence on the imaging capability of the imaging medical system. Furthermore, the limitations are increasingly narrowed to achieve more cost-effective imaging medical systems. If counteractive measures are not taken, this leads to a reduced image quality and therefore to a reduced diagnostic quality. Longer durations of measurement sequences can also be the result.

For a transmission (i.e. a transfer) of the measurement sequence from one medical imaging system to another medical imaging system with different (in particular reduced) capability it is known to scale a measurement sequence linearly with the capability of the transfer medical imaging system. This procedure does in fact (at least normally) lead to reliable and executable control sequences, but the control sequences are in many cases sub-optimal.

SUMMARY OF THE INVENTION

An object of the present invention is to determine optimized or nearly optimized control sequences for such a medical imaging system.

This object is achieved according to the invention by an operating method for a computer wherein the computer receives information about a measurement sequence to be implemented by an imaging medical system, the computer determines at least one group of preliminary control sequences for power control devices of the imaging medical system, the computer determines the preliminary control sequences of each group that cause the power control devices to control image-influencing emission devices of the imaging medical system according to measurement sequence to be implemented insofar as it concerns the control of the image-influencing emission devices, and wherein the computer respectively determines a load state curve for each group of preliminary control sequences using a model of at least the image-influencing emission devices and the power control devices using respective initial load states and the respective control sequences of the image-influencing emission devices and the power control devices. The computer checks for each group whether each load state curve determined for this group remains below a load limit. The computer outputs the preliminary control sequences of one of the groups whose determined load state curves remain below the load limits, as final control sequences.

For example, if a magnetic resonance system should be controlled with the measurement sequence, the x-, y- and z-gradient coils can each be an emission device. Each activated transmission antenna can furthermore be an additional emission device. The upstream power amplifiers correspond to power control devices. Each power control device is controlled with a respective control sequence. The entirety of the control sequences for the power amplifiers forms a group.

The control devices must be matched to one another so that they correspond in their entirety with the desired measurement sequence. If one of the control sequences of the group is changed, the other control sequences of the respective group must therefore (at least normally) be correspondingly adapted.

In an embodiment, in addition to the checking of the load state curves of the power control devices and of the emission devices, the computer determines the preliminary control sequences of each group such that a power supply device of the imaging medical system is caused to supply the power control devices with the energy required by the power control devices. The model also models the behavior of the power supply device. The computer also determines a respective load state curve for the power supply device for each group of preliminary sequences using the model with an initial load state of the power supply device and the control sequences.

The control sequences of one of the groups are advantageously the maximum possible control sequences. The maximum capability of the imaging medical system is used via this embodiment, in the event that it is possible.

In a preferred embodiment of the present invention, the computer first determines the load state curves for that group whose control sequences are the maximum possible control sequences, and checks whether each load state curve determined for this group remains below the respective load limit, and outputs the maximum possible control sequences as final control sequences in the event that the load state curves corresponding with the maximum possible control sequences remain below load limits.

Through this procedure, the computing effort to determine the final control sequences can be kept low.

The load state curves can be characteristic of the temperature of the respective modeled device, for example.

In a preferred embodiment of the present invention, the computer determines at least one of the load state curves (starting from the corresponding initial load state) by iterative addition of a load dependent on the momentary (current) control state of the respective modeled device and iterative subtraction of an unloading independent on the momentary (current) control state of the respective modeled device. This embodiment is relatively simple to implement. The implementation is possible even when an analytical solution is not possible.

The control sequence can be composed of a number of successive partial sequences that are identical or nearly identical to one another, and the computer can determine the load sum caused by each of the partial sequences once, and then can take the load sum into account in the determination of the corresponding load state curve. The computing effort can be reduced by this embodiment.

The computer advantageously determines for the first of the partial sequences a partial state curve that results up to the end of the first partial sequence. In this case, for example, it is possible that the computer adapts the partial sequences in the event that the maximum of the partial state curve for the first partial sequence is greater than the load limit. For example, the adaptation can be a reduction of a temporal stretching of the partial sequence or (without temporal stretching) a reduction of a power applied in the partial sequence.

Alternatively or additionally, the computer can determine an intermediate state resulting at the end of the first partial sequence and, beyond determining the intermediate state, takes additional measures only when the intermediate state is greater than the initial load state.

If the intermediate state is greater than the initial load state, for example, the computer can determine an estimated maximum load using the relation $$GMB=AZ+N \cdot (ZZ-AZ)+(MZ-ZZ),$$

wherein GMB is the estimated maximum load, AZ is the initial load state, N is the number of partial sequences, ZZ is the intermediate state and MZ is the maximum of the partial state curve. Beyond the determination of the estimated maximum load, additional measures are taken only if the estimated maximum load is greater than the load limit.

Alternatively or additionally, in the event that the unloading independent of the momentary control state of the modeled device is dependent on the momentary load state, the additional measures are a determination of partial state curves of additional partial sequences, and the taking of additional measures in the event of exceeding the load limit.

For example, the additional measures can be the insertion of a pause between two partial sequences in immediate succession and/or an adaptation of the partial sequences. As before, the adaptation can be a temporal stretching of the partial sequence or a reduction of an applied power.

In a preferred embodiment of the present invention, the computer is fashioned as a control device for the imaging medical system. In this case, the computer controls the imaging medical system corresponding to the final control sequences.

The imaging medical system can be fashioned as a magnetic resonance system. In this case, the power control devices are gradient power amplifiers, the image-influencing emission devices are gradient coils. If necessary, the power control devices can also include at least one radio-frequency power amplifier and the image-influencing emission devices include at least one radio-frequency transmission antenna.

The above object also is achieved in accordance with the present invention by a computer-readable medium encoded with programming instructions which, when the medium is loaded into a computer or processor, cause the computer or processor to execute and/or implement the method described above, including all embodiments and variance.

In terms of the system, the above object is achieved by a medical imaging system having power control devices and image-influencing emission devices controlled by the power control devices, and a control device connected with at least the power control devices, with the control device being a computer configured according to the invention, or being connected with a computer configured according to the invention.

BRIEF DESCRIPTION OF THE DRAWINGS

FIG. 1 is a block diagram schematically illustrating a first embodiment of a medical imaging system in accordance with the present invention.

FIG. 2 is a block diagram schematically illustrating a second embodiment of a medical imaging system in accordance with the present invention.

FIG. 3 is a flowchart showing the basic steps of an embodiment of the inventive method.

FIG. 9 is a block diagram schematically illustrating a sixth embodiment of a medical imaging system in accordance with the present invention.

FIG. 10 is a block diagram schematically illustrating a seventh embodiment of a medical imaging system in accordance with the present invention.

DESCRIPTION OF THE PREFERRED EMBODIMENTS

Figure 4:
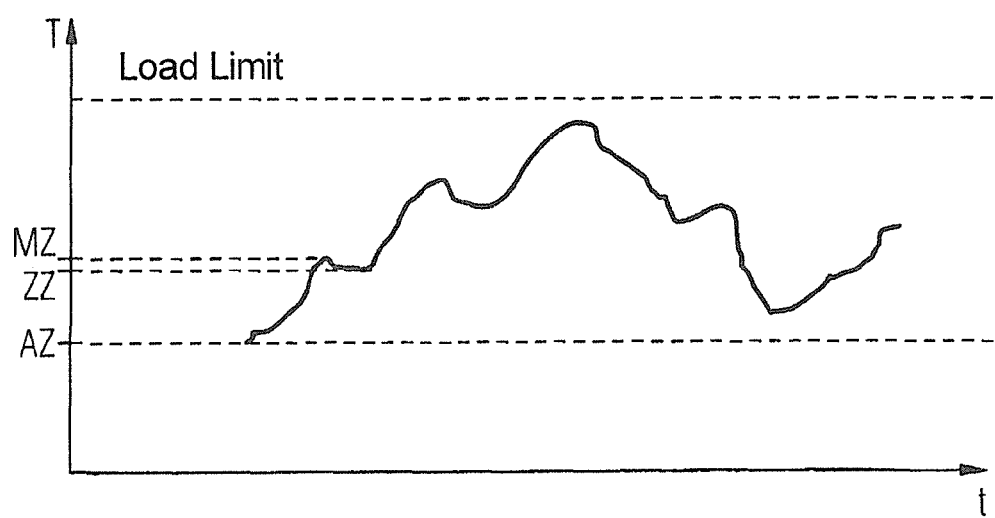
FIG. 4 is a time diagram for assisting in explanation of the invention.

The present invention is subsequently explained in connection with a magnetic resonance system, but the procedures and embodiments according to the invention are also possible for use in other imaging medical systems, for example in C-arm x-ray systems, in CT systems, in ultrasound tomography systems, etc.

According to FIGS. 1 and 2, the imaging medical system has power control devices and image-influencing emission devices. In the embodiment according to FIGS. 1 and 2, in which the imaging medical system is fashioned as a magnetic resonance system, the power control devices are at least gradient power amplifiers 1. The image-influencing emission devices are at least gradient coils 3. The power control devices can also include at least one radio-frequency power amplifier 2. The image-influencing emission devices in this case can include at least one radio-frequency transmission antenna 4.

The imaging medical system furthermore has a control device 5. The control device 5 is connected with at least the power control devices 1, 2. It can additionally be connected with the emission devices. The control device 5 is normally fashioned as a software-programmable control device 5, but this is of subordinate importance in the framework of the present invention.

It is possible for the control device 5 to be fashioned purely as a control device. This case is shown in FIG. 1. In this case, the control device 5 is connected with a computer 6. Alternatively, it is possible that the control device 5 is fashioned as such a computer 6. This embodiment is shown in FIG. 2.

In the following, the description the computer 6 and its mode of operation (including the interaction with the control device 5) is associated with FIGS. 3 through 10. In the event that the control device 5 is fashioned as a computer 6, the statements regarding the data exchange between the computer 6 and the control device 5 naturally do not apply.

The computer 6 is software-programmable. In operation it executes a computer program 7 that is stored in a control device 8 of the computer 6. The computer program 7 comprises machine code 9 that can be directly executed by the computer 6. The execution of the machine code 9 by the computer 6 has the effect that the computer 6 executes an operating method that is subsequently explained in detail.

The computer program 7 can have been supplied to the computer 6 in various ways. For example, it is possible to supply the computer program 7 to the computer 6 via a connection to a computer network (for example the Internet or a LAN). Alternatively, it is possible to store the computer program 7 on a data medium 10 and to supply the computer program 7 to the computer 6 via the data medium 10. The data medium 10 can be fashioned as needed. A CD-ROM is presented in FIGS. 1 and 2. However, the data medium 10 could alternatively be fashioned as a USB memory stick or as a memory card, for example.

As already mentioned, the execution of the computer program 7 by the computer 6 causes the computer 6 to implement an operating method. The operating method is subsequently explained in detail in connection with FIG. 3.

According to FIG. 3, the computer 6 receives information in Step S1. The information is at least information about a measurement sequence that should be implemented by the imaging medical system. Furthermore, the information can be information about initial load states AZ of the power control devices 1, 2 and of the emission devices 3, 4. The computer 6 normally receives the information from the control device 5. Alternatively, the computer 6 can receive the information from a user 11. Combinations of these are also possible.

Furthermore, in the framework of Step S1 the computer 6 can receive information about the capability of the power control devices 1, 2 and/or of the emission devices 3, 4. Examples of possible capabilities are a possible rise time, a possible rise slope, a saturation current etc. Information about load limits can also be provided to the computer in Step S1.

In the event that the information about the initial load states AZ is not provided in Step S1, the initial load states AZ must be otherwise known to the computer 6, for example be hard-set. In this case, the initial load states AZ must be reasonably defined. A conservative estimation is normally sufficient for this. Analogous statements apply for the load limits.

In Step S2, the computer 6 determines at least one group of preliminary control sequences for the power control devices 1, 2. The computer 6 hereby determines the preliminary control sequences of each group that cause (or will cause) the power control devices 1, 2 to control the image-influencing emission devices 3, 4 according to the respective preliminary control sequences. The determination is furthermore such that the control of the image-influencing emission devices 3, 4 corresponds with the measurement sequence to be implemented, by means of the respective control sequences of the respective group. The latter statement naturally applies only insofar as it pertains to the control of the image-influencing emission devices 3, 4. The determinations of Step S2 ensue independently of whether the power control devices 1, 2 and the emission devices 3, 4 maintain their respective load limits.

Insofar as additional devices (for example diaphragms or receivers) must be controlled in the framework of the measurement sequence, this activation is naturally conducted in the framework of the execution of the measurement sequence, but it is not the subject matter of the present invention.

It is always possible to determine multiple groups of preliminary control sequences in the framework of Step S2. An example is subsequently explained in which it can, in many cases, be sufficient to determine only a single group of preliminary control sequences.

In Step S3, the computer 6 determines a load state curve for each group of preliminary control sequences using a model 12 of the imaging medical system with the respective initial load state AZ and the respective control sequence. For each power control device 1, 2, the computer 6 thus determines the load state curve therefor using the corresponding control sequence and the corresponding initial load state AZ. Furthermore, for each emission device 3, 4 the computer 6 determines the load state curve therefor using the initial load state AZ for that emission device 3, 4 and the control sequence with which the associated power control device 1, 2 is operated.

The load can be selected as needed. It can be characteristic of the temperature T of the respectively modeled device 1 through 4 (see FIG. 4).

In Step S4, the computer 6 checks for each group whether each load state curve determined for this group remains below a load limit. The load limit can hereby be individual to the respective modeled device 1 through 4.

In Step S5, the computer 6 determines as final control sequences the preliminary control sequences of one of the groups whose determined load state curves remain below the load limits. It furthermore outputs the final control sequences in Step S6.

If the computer 6 is identical with the control device 5, the output ensues directly at the corresponding power control devices 1, 2. In this case, the computer 6 controls the imaging medical system corresponding to the final control sequences. If the computer 6 and the control device 5 are different (separate) from one another, the computer 6 outputs the final control sequences, normally directly to the control device 5, so that this can subsequently directly affect the corresponding control of the power control devices 1, 2.

It is possible for the model 12 to model only the power control devices 1, 2 and the emission devices 3, 4. In this case, the load state curves are naturally determined only for the devices 1 through 4. This procedure is shown in FIG. 3. The model 12, however, also can model the behavior of a power supply device 13 from which the power control devices 1, 2 are commonly supplied with power. In this case, the procedure of FIG. 3 is modified corresponding to FIG. 5.

Figure 5:
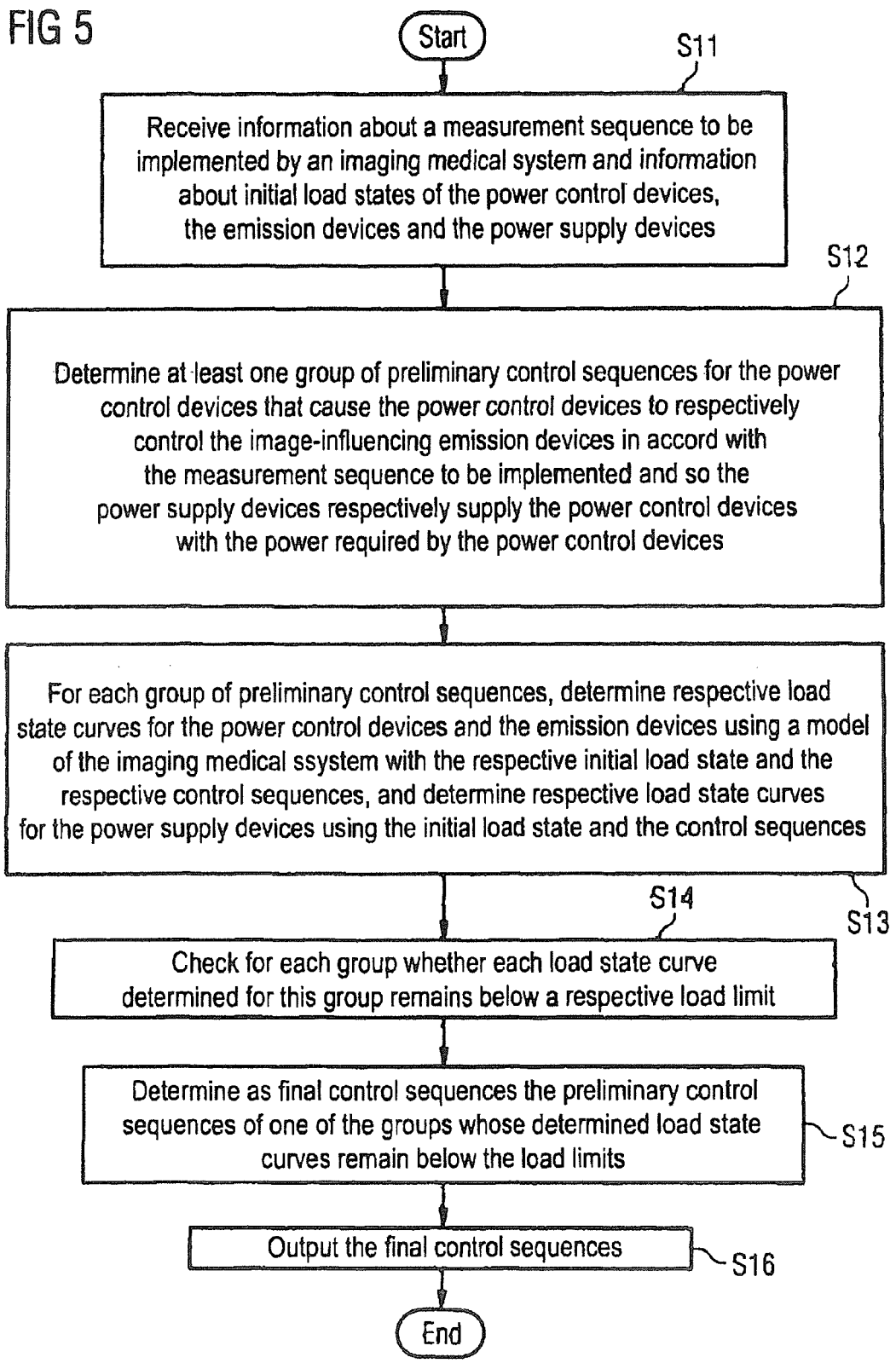
FIG. 5 is a block diagram schematically illustrating a third embodiment of a medical imaging system in accordance with the present invention.

According to FIG. 5, the computer 6 executes Steps S11 through A16. Steps S11 through S16 essentially correspond with the Steps S1 through S6 from FIG. 3 with the following differences.

In Step S11 the computer 6 can also receive information about an initial load state and a load limit of the power supply device 13. Alternatively, this information can be permanently present in the computer 6. In Step S12, the computer 6 determines the preliminary control sequences of each group such that the power supply device 13 is in the position to supply the power control devices 1, 2 with the power required by said power control devices 1, 2. In Step S13, the computer 6 also additionally determines a respective load state curve for the power supply device 13 for each group of preliminary control sequences using the model 12 with the initial load state of the power supply device 13 and the control sequences.

A determination of optimal control sequences should ensue based on the operating method according to the invention. For this reason it is preferred that the control sequences of one of the groups are the maximum possible control sequences, The term "maximum possible control sequences" means that only the capability of the power control devices 1, 2, of the emission devices 3, 4 and—insofar as it is taken into account—of the power supply device 13, are considered in the determination of these control sequences. The load of the respective devices 1 through 4, 13 still remains unconsidered in the determination of these control sequences.

The last described procedure is therefore in particular preferred because the capability of the imaging medical system can be completely utilized in the event that the maximum possible control sequences are reliable, i.e. the load limits are not exceeded. Furthermore, the computing effort can be kept as low as possible in that it is first determined whether the maximum possible control sequences exceed the load limits. If the maximum possible control sequences are also reliable, an additional calculation is invalid.

Figure 6:
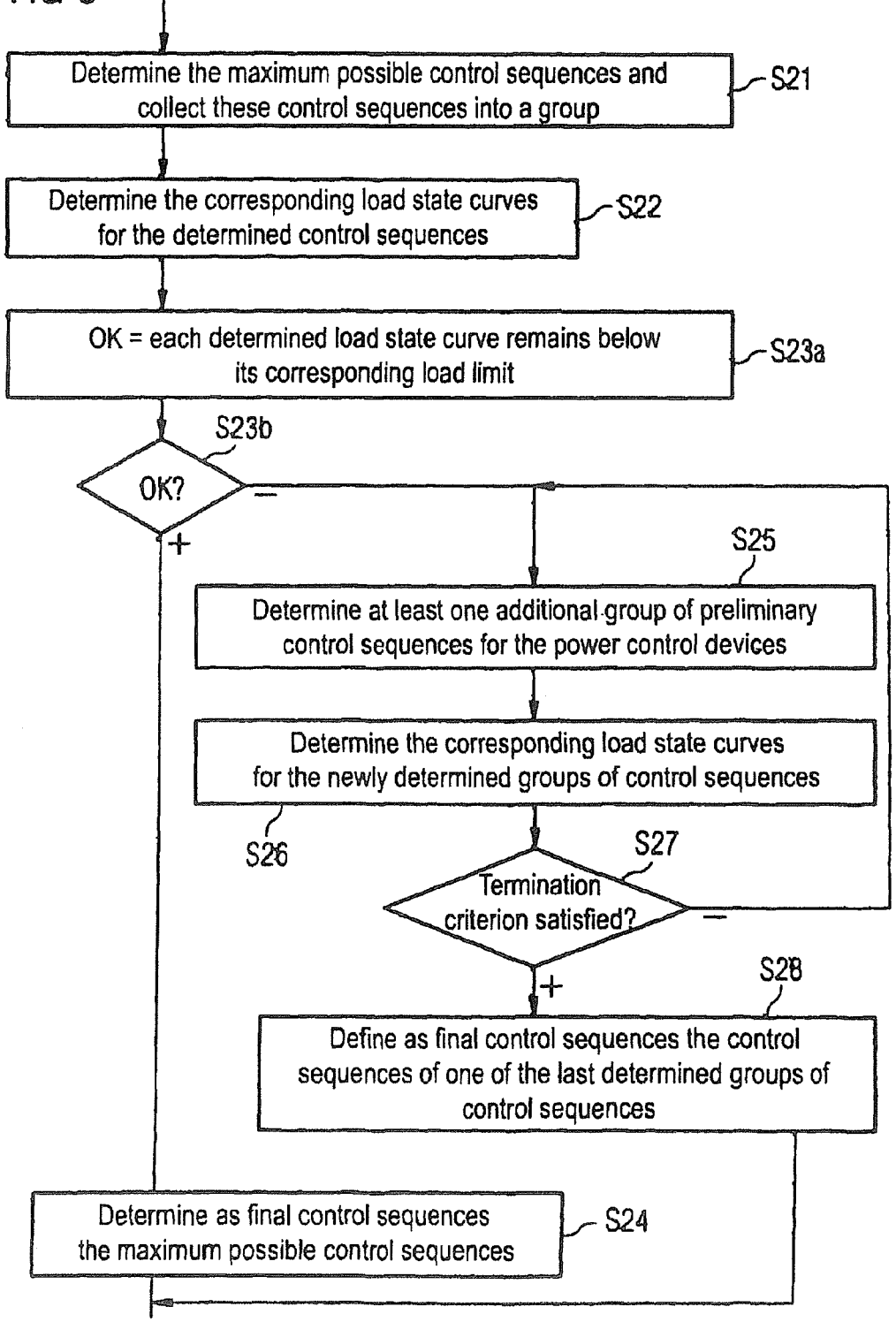
FIG. 6 is a block diagram schematically illustrating a fourth embodiment of a medical imaging system in accordance with the present invention.
Figure 7:
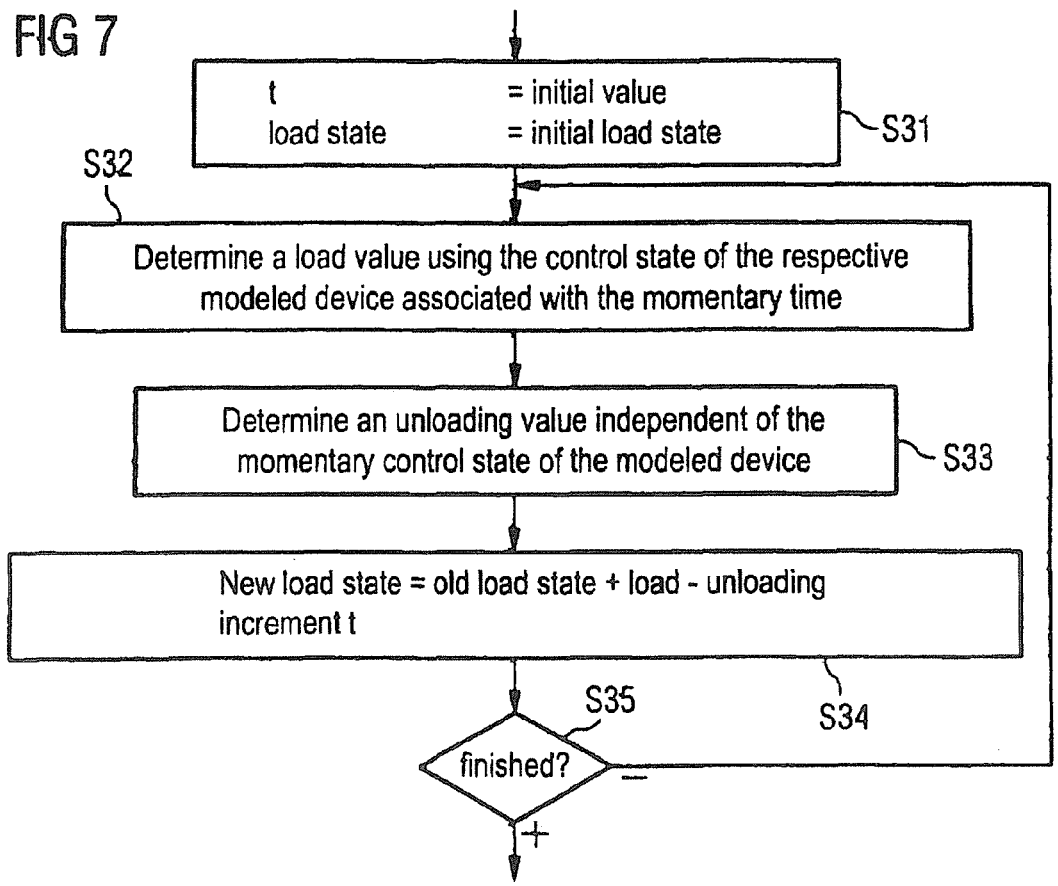
FIG. 7 is a block diagram schematically illustrating a fifth embodiment of a medical imaging system in accordance with the present invention.

In a preferred embodiment of the present invention, Steps S3 through S5 from FIG. 3 (or, respectively, alternatively Steps S13 through S15 from FIG. 5) are therefore designed corresponding to FIG. 6.

According to FIG. 6, in Step S21 the computer 6 initially determines the maximum possible control sequences and assembles these control sequences into a group. The determination of the maximum possible control sequences ensues corresponding to the limit conditions explained in the preceding in connection with Steps S2 or, respectively, S12.

In Step S22, the computer 6 determines the corresponding load state curves for the control sequences determined in Step S21.

In Step S23, the computer 6 checks whether each determined load state curve remains below its corresponding load limit. If this is the case, the computer 6 transitions to Step S24. In Step S24, the computer 6 determines the maximum possible control sequences as final control signals and outputs them. Step S23 is presented in two sub-steps S23a and S23b in FIG. 6 for clarity.

If (at least) one of the determined load state curves exceeds its corresponding load limit, the computer 6 transitions to Step S25. In Step S25, the computer 6 determines at least one addition group of preliminary control sequences for the power control devices 1, 2. The determination of Step S25 hereby ensues again under consideration of the limit conditions; see the explanations regarding Steps S2 and S12.

In Step S26, the computer 6 determines the corresponding load state curves for the groups of control sequences determined in Step S25.

In Step S27, the computer 6 checks whether a termination criterion is satisfied. The termination criterion can be satisfied only when the load state curves of one of the groups of control sequences determined in Step S25 remain below their corresponding load limits. Otherwise, the computer 6 returns to Step S25.

If the termination criterion is satisfied, the computer 6 transitions to Step S28. In Step S28, the computer 6 defines as final control sequences the control sequences of one of the groups of control sequences determined in the last pass of Step S25 and outputs these final control sequences.

In a practical embodiment of the Steps S25 through S28, for example, the computer 6 can determine the optimized control sequences in which the load limits are still maintained bit by bit via interval division or similar procedures.

The model 12 may contain analytical solutions for determining the load state curves, but it is normally not possible to determine such analytical solutions. If such an analytical solution is not possible, the computer 6 determines a numerical solution by means of the model 12. In this case the computer 6 divides the control sequences into small time segments and proceeds as is subsequently explained in detail in connection with FIG. 7 for a single load state curve.

According to FIG. 6, in Step S31 the computer 6 sets a time t to an initial value and a load state to an initial load state AZ. In Step S32, the computer 6 determines a load value using the control state of the respective modeled devices 1 through 4, 13 associated with the current time t. Furthermore, in Step S33 the computer 6 determines an unloading value. The unloading value is independent of the momentary control state of the modeled devices 1 through 4 but it can depend on the momentary load state of the modeled devices 1 through 4 and 13. In Step S34, the computer 6 adds the load determined in Step S32 to a momentary load state and subtracts the unloading determined in Step S33. Furthermore, the computer 6 increments the time t in Step S34.

In Step S35, the computer 6 checks whether it has already determined the entire load state curve. If this is not the case, the computer returns to Step S32.

Figure 8:
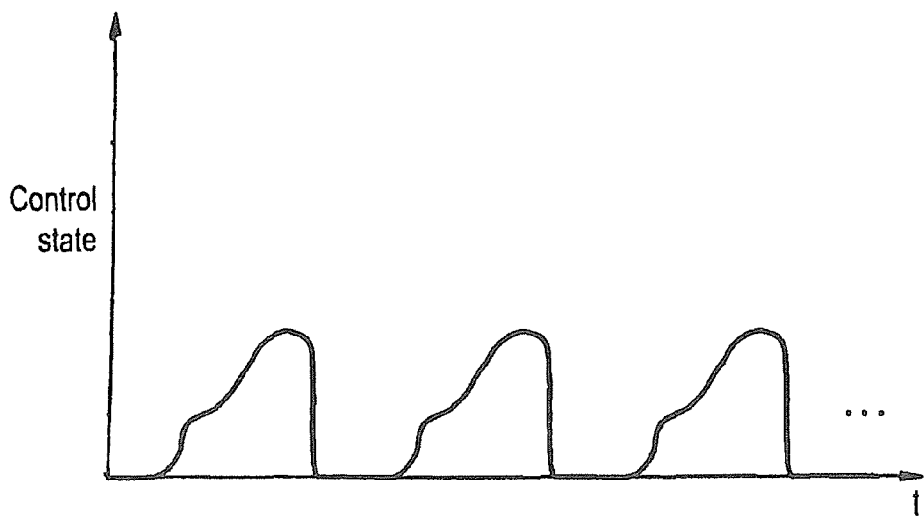
FIG. 8 is a time diagram for explaining the further embodiments of the present invention.

In many cases, the control sequences are composed of a number of partial sequences; as is shown in the example of FIG. 8 for a single control sequence. According to FIG. 8, the partial sequences are identical or at least nearly identical among one another and regularly follow one another. In this case the procedure from FIG. 7 can be designed corresponding to FIG. 9.

According to FIG. 9, it is possible for the computer 6 to select the first (chronologically speaking) partial sequence in Step S42 and to determine a partial state curve in Step S43. The partial state curve extends up to the end of the selected partial sequence.

In Step S44, the computer 6 checks whether it has already implemented Step S43 for all partial sequences. If this is not the case, the computer 6 transitions to Step S45. In Step S45, the computer 6 selects the next partial sequence. It then returns to Step S43. Otherwise, the method is terminated according to FIG. 9.

A procedure that is subsequently explained in detail in connection with FIG. 10 is particularly preferred. According to FIG. 10, Step 41 is likewise present, but the further workflow is different from the workflow according to FIG. 9.

According to FIG. 10, Step S51 is executed next. In Step S51, the computer 6 determines the partial state curve up to the end of the first partial sequence, analogous to Step S43.

In Step S52, the computer 6 determines a maximum MZ of the partial state curve for the first partial sequence. Furthermore, in Step S53 the computer 6 checks whether the maximum MZ is greater than the corresponding load limit. If this is the case, the computer 6 transitions to Step S54. In Step S54, the computer 6 adapts the partial sequences. The computer 6 can in particular temporally extend the partial sequences in the framework of Step S54.

If the maximum MZ lies below the load limit, the computer 6 transitions to Step S55. In Step S55, the computer 6 checks whether an intermediate state ZZ resulting at the end of the first partial sequence is greater than the corresponding initial load state AZ. If this is not the case, it is possible without any additional measures to execute the entire control sequence. Otherwise, the computer 6 takes further measures. Multiple cases are hereby presented in FIG. 10. However, the cases can be realized independent of one another.

One possibility is to execute Step S56. In Step S56 the computer 6 determines an estimated maximum load GMB.

The computer 6 hereby advantageously determines the estimated maximum load using the relationship $$GMB=AZ+N\cdot(ZZ-AZ)+(MZ-ZZ).$$

N is the number of partial sequences. The other variables occurring in the relationship above are already defined.

In Step S57, the computer 6 checks whether the estimated maximum load GMB is greater than the respective load limit. If this is not the case, it is possible without further measures to control the appertaining modeled device 1 through 4, 13 corresponding to the respective control sequence. Additional measures are therefore not necessary.

Otherwise, the computer 6 can transition to Step S58. The computer 6 takes additional measures in Step S58. The additional measures can hereby in particular comprise an insertion of a pause between each two immediately successive partial sequences. Alternatively or additionally, the additional measures can comprise an adaptation of the partial sequences (in particular a temporal extension of the partial sequences or a reduction of the applied power).

The procedure according to Steps S56 and S57 always leads to allowable control sequences, but it is possible that the control sequences may not be optimally selected. In particular, the momentary unloading is normally dependent on the momentary load state. For example, a cooling body by means of which one of the power control devices 1, 2 is cooled emits more heat the warmer that it is. However, in this case a conservative estimation results in Step S56 to stay on the safe side.

Steps S59 and S60 can be present as an alternative or in addition to Steps S56 and S57. Steps S59 and S60 are meaningful in the event that the momentary unloading of the respective modeled devices 1 through 4, 13 is in fact independent of the momentary control state of the modeled device 1 through 4, 13 but is dependent on the momentary load state of the modeled device 1 through 4, 13.

In Step S59, the computer 6 determines the partial state curves of additional partial sequences. A successive determination of only individual successive partials state curves or a determination of all partial state curves (thus for the entire control sequence) is hereby alternatively possible.

In Step S60, the computer 6 checks whether the partial state curves determined in Step S58 exceed the corresponding load limit. If this is the case, the computer 6 transitions to Step S57. Otherwise—assuming that the entire load state curve has already been determined—the method from FIG. 10 is ended.

The present invention has many advantages. In particular, it is possible in a simple manner to determine optimal or, respectively, at least nearly optimal control sequences for the power control devices 1, 2 of the imaging medical system.

Although modifications and changes may be suggested by those skilled in the art, it is the intention of the inventor to embody within the patent warranted hereon all changes and modifications as reasonably and properly come within the scope of his contribution to the art.

I claim as my invention:

1. An operating method for a computer that operates a medical imaging system, comprising the steps of:
    importing information into said computer describing a measurement sequence to be implemented by said medical imaging system, said medical system comprising a plurality of power control devices that respectively control a plurality of image-influencing emission devices;
    prior to implementing said measurement sequence by said medical imaging system, automatically determining, in said computer, at least one group of preliminary control sequences, wherein each preliminary control sequences in said group is a control sequence for one of said power control devices, each preliminary control sequence being designed to cause the power control device for which that preliminary control sequence is determined, when said measurement sequence is implemented, to control the image-influencing emission device controlled by that power control device in accordance with the preliminary control sequence;
    in said computer, for each group of preliminary control sequences, automatically determining a load state curve that is applicable to the respective group, using a model that models the image-influencing emission devices and that models the power control devices, and using an initial load state and the respective preliminary control sequences;
    in said computer, automatically checking, for each group of preliminary control sequences, whether the load state curve determined therefor remains below a load limit that is applicable to the respective group;
    in said computer, determining the preliminary control sequences of one of said groups which has a load state curve below said load limit as final control sequences; and
    after determining said first control sequences, employing said computer as a control device for said medical imaging system, and from said computer, operating as said control device, controlling operation of said medical imaging system to execute said measurement sequence, including emitting said final control sequences as an output from said computer and controlling the respective power control devices according to said final control sequences.

2. An operating method as claimed in claim 1 wherein said medical imaging system comprises a power supply device that supplies power to the plurality of power control devices, and wherein said method comprises:
    in said computer, determining said preliminary control sequences for each group to cause the power supply device for the power control devices to supply power to the power control devices with a power required by said power control devices according to the preliminary control sequence;
    in said computer, also basing said model on operation of the respective power supply devices for the power control devices in each group; and
    in said computer, determining said load state curve for the power supply devices for each group using said model with the initial load state being for the respective power supply devices.

3. An operating method as claimed in claim 1 comprising, in said computer, determining said load state curves to represent respective temperatures of the power control devices and the image-influencing emission devices in said model.

4. An operating method as claimed in claim 1 comprising in said computer, generating one group of preliminary control sequences as maximum possible control sequences.

5. An operating method as claimed in claim 4 comprising, in said computer, initially determining said load state curves for a group having control sequences as control sequences representing maximum possible control sequences and checking whether each load state curve remains below the respective load limit, and emitting the maximum possible control sequences as said final control sequences if said load state curves for the maximum power control sequences remain below said load limit.

6. An operating method as claimed in claim 1 comprising in said computer, determining said load state curves as representing respective temperatures of said power control devices and said image-influencing emission devices in said model.

7. An operating method as claimed in claim 1 comprising, in said computer, determining at least one of said load state curves by starting with an initial load state and iteratively adding a load thereto dependent on respective momentary preliminary control states of said power control devices and said image-influencing emission devices in said model, and by iteratively subtracting unloading independently of said momentary control state.

8. An operating method as claimed in claim 7 comprising, in said computer, determining said control sequence as a plurality of successive partial sequences that are substantially identical with each other and, in said computer, determining one load sum caused by each of said partial sequences and using said load sum to determine the corresponding load state curve.

9. An operating method as claimed in claim 8 comprising, in said computer, for a first of said partial sequences, determining a partial state curve that results up to an end of said first of said partial sequences.

10. An operating method as claimed in claim 9 comprising, in said computer, adapting said partial sequences if a maximum of said partial state curve for said first of said partial sequences is larger than said load limit.

11. An operating method as claimed in claim 9 comprising, in said computer, determining an intermediate state that results at said end of said first of said partial sequences and beyond said end of said first of said partial sequences and making further calculations concerning the respective preliminary control sequence only if said intermediate state is larger than said initial load state.

12. An operating method as claimed in claim 11 comprising, in said computer, if said intermediate state is larger than said initial load state, automatically determining an estimated maximum load GMB using the relation $$GMB = AZ + N \cdot (ZZ - AZ) + (MZ - ZZ),$$

wherein AZ is the initial load state, N is the number of partial sequences, ZZ is the intermediate state, and MZ is the maximum of the partial state curve and, that said computer making further calculations concerning the respective preliminary control sequence only if said estimated maximum load GMB is greater than said load limit.

13. An operating method as claimed in claim 11 comprising, in said computer, if said unloading, that is independent of the momentary control state, is dependent on said momentary load state, implementing said additional calculations as determining respective partial state curves for the partial sequences beyond said first of said partial sequences.

14. An operating method as claimed in claim 11 comprising, in said computer, inserting a pause between two of said partial sequences in immediate succession, or adapting the partial sequences.

15. An operating method as claimed in claim 1 comprising employing a magnetic resonance system as said medical imaging system, that comprises gradient power amplifiers forming said power control devices and gradient coils as said image-influencing emission devices.

16. An operating method as claimed in claim 15 comprising additionally employing, in said power control devices, at least one radio-frequency power amplifier, and additionally employing, in said image-influencing emission devices, at least one radio-frequency transmission antenna supplied with power by said at least one radio-frequency power amplifier.

17. A non-transitory computer-readable medium encoded with programming instructions for a computer that operates a medical imaging system that comprises a plurality of power control devices that respectively control a plurality of image-influencing emission devices, said computer having information imported therein describing a measurement sequence to be implemented by said medical imaging system, said programming instructions causing said computer to:

prior to implementing said measurement sequence by said medical imaging system, automatically determine at least one group of preliminary control sequences, wherein each preliminary control sequences in said group is a control sequence for one of said power control devices, each preliminary control sequence being designed to cause the power control device for which that preliminary control sequence is determined, when said measurement sequence is implemented, to control the image-influencing emission device controlled by that power control device in accordance with the preliminary control sequence;

for each group of preliminary control sequences, automatically determine a load state curve that is applicable to the respective group, using a model that models the image-influencing emission devices and that models the power control devices and using an initial load state and the respective preliminary control sequences;

automatically check, for each group of preliminary control sequences, whether the load state curve determined therefor remains below a load limit that is applicable to the respective group, automatically determine, as final control sequences, the preliminary control sequences of one of said groups that has a load state curve below said load limit; and after determining said final control sequences, operate said computer as a control device for said medical imaging system, and from said computer, operating as said control device, control operation of said medical imaging system to execute said measurement sequence, including emitting said final control sequences as an output from said computer and controlling the respective power control devices according to said final control sequences.

18. A computer that operates a medical imaging system that comprises a plurality of power control devices that respectively control a plurality of image-influencing emission devices, said computer having information imported therein describing a measurement sequence to be implemented by said medical imaging system, said computer being programmed to:

automatically determine at least one group of preliminary control sequences respectively for said power control devices, each preliminary control sequence causing the power control device for which that preliminary control sequence is determined to control the image-influencing emission device controlled by that power control device in accordance with the preliminary control sequence to cause said plurality of image-influencing emission devices, in combination, to implement said measurement sequence;

for each group of preliminary control sequences, automatically determine a load state curve using a model of the image-influencing emission devices and the power control devices and using an initial load state and the respective preliminary control sequences;

automatically check, for each group of preliminary control sequences, whether the load state curve determined therefor remains below a load limit;

automatically determine control sequences as being a preliminary control sequence in said group that has a load state curve below said load limit, and emitting said final control sequences as an output from said computer respectively to said power control devices to operate said power control devices according to said final control sequences; and prior to implementing said measurement sequence by said medical imaging system, automatically determine at least one group of preliminary control sequences, wherein each preliminary control sequences in said group is a control sequence for one of said power control devices, each preliminary control sequence being designed to cause the power control device for which that preliminary control sequence is determined, when said measurement sequence is implemented, to control the image-influencing emission device controlled by that power control device in accordance with the preliminary control sequence;

for each group of preliminary control sequences, automatically determine a load state curve that is applicable to the respective qroup, using a model that models the image-influencing emission devices and that models the power control devices and using an initial load state and the respective preliminary control sequences;

automatically check, for each group of preliminary control sequences, whether the load state curve determined therefor remains below a load limit that is applicable to the respective group, automatically determine, as final control sequences, the preliminary control sequences of one of said groups that has a load state curve below said load limit; and after determining said final control sequences, operate said computer as a control device for said medical imaging system, and from said computer, operating as said control device, control operation of said medical imaging system to execute said measurement sequence, including emitting said final control sequences as an output from said computer and controlling the respective power control devices according to said final control sequences.

19. A medical imaging system comprising:
a plurality of power control devices that respectively control a plurality of image-influencing emission devices; and a computer having information imported therein describing a measurement sequence to be implemented by said medical imaging system, said computer being configured to automatically determine prior to implementing said measurement sequence by said medical imaging system, at least one group of preliminary control sequences, wherein each preliminary control sequences in said group is a control sequence for one of said power control devices, each preliminary control sequence being designed to cause the power control device for which that preliminary control sequence is determined, when said measurement sequence is implemented, to control the image-influencing emission device controlled by that power control device in accordance with the preliminary control sequence, and to automatically determine, for each group of preliminary control sequences, a load state curve that is applicable to the respective group, using a model that models the image-influencing emission devices and that models the power control devices and using an initial load state and the respective preliminary control sequences, and to automatically check, for each group of preliminary control sequences, whether the load state curve determined therefor remains below a load limit that is applicable to the respective group, and to automatically determine as final control sequences, the preliminary control sequences as one of said groups that has a load state curve below said load limit, and, after determining said final control sequences, operate as a control device for said medical imaging system, and from said computer, operating as said control device, control operation of said medical imaging system to executed said measurement sequence, including emitting said final control sequence as an output from said computer and controlling the respective power control devices according to said final control sequences.

* * * * *